US009833752B2

(12) United States Patent
Wuenn et al.

(10) Patent No.: US 9,833,752 B2
(45) Date of Patent: Dec. 5, 2017

(54) RADIATION-RESISTANT MICROPOROUS MEMBRANE HAVING A HYDROPHOBICITY GRADIENT

(75) Inventors: Eberhard Wuenn, Goettingen (DE); Tobias Schleuss, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 219 days.

(21) Appl. No.: 13/813,512

(22) PCT Filed: Aug. 9, 2011

(86) PCT No.: PCT/EP2011/003971
§ 371 (c)(1),
(2), (4) Date: Jan. 31, 2013

(87) PCT Pub. No.: WO2012/031653
PCT Pub. Date: Mar. 15, 2012

(65) Prior Publication Data
US 2013/0139685 A1   Jun. 6, 2013

(30) Foreign Application Priority Data

Sep. 7, 2010   (DE) .................. 10 2010 044 648

(51) Int. Cl.
| | | |
|---|---|---|
| B01D 53/22 | (2006.01) | |
| B01D 71/68 | (2006.01) | |
| B01D 61/00 | (2006.01) | |
| B01D 67/00 | (2006.01) | |
| B01D 69/02 | (2006.01) | |
| A61L 9/16 | (2006.01) | |

(52) U.S. Cl.
CPC ........... *B01D 71/68* (2013.01); *B01D 53/228* (2013.01); *B01D 61/00* (2013.01); *B01D 67/0093* (2013.01); *B01D 69/02* (2013.01); *A61L 9/16* (2013.01); *B01D 2323/30* (2013.01); *B01D 2325/28* (2013.01); *B01D 2325/38* (2013.01)

(58) Field of Classification Search
CPC ...... B01D 53/228; B01D 71/68; B01D 61/00; B01D 67/0093; B01D 69/02; B01D 2323/30; B01D 2325/28; B01D 2325/38; B01D 19/0031; A61L 9/16; A61L 9/18
USPC ........... 95/45, 46; 96/4, 14; 427/244; 521/27
See application file for complete search history.

(56) References Cited

U.S. PATENT DOCUMENTS 4,954,256 A * 9/1990 Degen et al. .................. 210/490
5,171,439 A * 12/1992 Vakharia ............ B01D 19/0031
                                                                210/436

(Continued)

FOREIGN PATENT DOCUMENTS

| WO | 2005/048388 | 5/2005 |
| WO | 2009/065092 | 5/2009 |
| WO | 2009/086347 | 7/2009 |

OTHER PUBLICATIONS

International Preliminary Report on Patentability, 2013.
International Search Report of Nov. 16, 2011.

*Primary Examiner* — Jason M Greene
(74) *Attorney, Agent, or Firm* — Gerald E. Hespos; Michael J. Porco; Matthew T. Hespos

(57) ABSTRACT

The present invention relates to a radiation-resistant microporous membrane having a hydrophobicity gradient, to a method for the preparation thereof, and to the use of the membrane in the sterilizing filtration of gaseous fluids or as a liquid barrier in liquid-containing systems to be vented.

12 Claims, 2 Drawing Sheets

(56) References Cited

U.S. PATENT DOCUMENTS

| | | | |
|---|---|---|---|
| 5,403,483 A * | 4/1995 | Hayashida et al. | 210/490 |
| 5,554,414 A * | 9/1996 | Moya et al. | 427/244 |
| 6,579,342 B2 | 6/2003 | Wang et al. | |
| 8,133,306 B2 * | 3/2012 | Quayle et al. | 96/4 |
| 2007/0154703 A1 * | 7/2007 | Waller et al. | 428/319.3 |
| 2008/0237117 A1 | 10/2008 | Bansal et al. | |
| 2010/0086438 A1 * | 4/2010 | Larsson et al. | A61L 2/07 422/26 |
| 2010/0261801 A1 * | 10/2010 | Weiss et al. | 521/27 |
| 2011/0091698 A1 * | 4/2011 | Zhou et al. | 428/212 |

* cited by examiner

RADIATION-RESISTANT MICROPOROUS MEMBRANE HAVING A HYDROPHOBICITY GRADIENT

BACKGROUND OF THE INVENTION

1. Field of the Invention

The present invention relates to a radiation-resistant microporous membrane having a hydrophobicity gradient, to a method for the preparation thereof, to the use of the membrane in the sterilizing filtration of gaseous fluids and to the use of the membrane as a liquid barrier in liquid-containing systems to be vented.

2. Description of the Related Art

In the fields of foodstuff and pharmaceutical manufacturing and of biotechnological production and in healthcare, sterile operations are a prerequisite for commercial success. For pathogen-free operations, it is important not only that solutions to be processed are sterile, but also that work equipment and manufacturing equipment are pathogen-free. The latter group includes preparation, mixing, transport or storage tanks made of metal, glass or plastic, and also reactors and fermenters, more particularly those having flexible plastic walls for single use.

Customary process steps in the industrial operation of reusable metal containers are cleaning and sterilization using superheated steam, filling, temperature adjustment, transport and emptying of liquids. With the exception of the cleaning step, the processes mentioned require a sterile-filtering venting element (venting device) at at least one tank opening (a flange) in order to prevent damage to the manufacturing equipment due to elevated or reduced pressure and, at the same time, to ensure that the solution-contacted interior is pathogen-free during venting.

The venting element is the interface between a preferably sterile, liquid-containing tank interior (e.g. as a liquid barrier in dialysis devices, infusion solution tanks or in fermenters) and an external, preferably nonsterile atmosphere. The actual partition medium selected in the venting element is, in most cases, a sterile-filtering membrane filter composed of a synthetic polymer. In rare cases, a nonwoven composed of synthetic fibrous material is incorporated.

In most cases, synthetic polymers have hydrophobic surface properties which can be attributed to the intrinsic hydrophobicity of the synthetic materials. The hydrophobicity is a material constant. It is caused by the extramolecular interactions of the atom groups forming the polymer.

Surfaces having a contact angle of more than 90° with respect to water are referred to as hydrophobic. Hydrophobic substances are not miscible or wettable with water. The substances are usually nonpolar. Their surface tension at 20° C. is below 72 mN/m.

The hydrophobic character of the sterile-filtering partition medium is a prerequisite for incorporation into a venting element for two different reasons. Firstly, a closed water film must not form on the surface of or within the partition medium upon contact with water or medium or, more particularly, water vapor (when steaming or gassing bioreactors). The water film would prevent pressure equalization (gas exchange) between the internal and external atmosphere and, as a result, compromise the mechanical integrity of the tank. In this case, it is advantageous when the partition medium exhibits strong hydrophobicity (e.g. as in the case of fluorine-containing organic polymers) through to an oleophobic character.

In the case of venting applications, use is made of customary materials for membrane filters, such as polytetrafluoroethylene (PTFE), polypropylene (PP) and polyvinylidene fluoride (PVDF), and in the case of fibrous material, use is made of polyethylene (PE).

Secondly, a hydrophobic partition medium allows wetting with simple organic solvents (e.g. alcohol) in order to check the integrity of the partition medium before and after use. The partition medium is checked by means of the pressure-hold test and/or the bubble-point test. For the pressure-hold test, pressure is applied to the wetted membrane. For this purpose, up to about 80% of the bubble-point value to be expected is selected for example. This pressure is subsequently observed for a few minutes. During this time, the pressure drop must not exceed a particular limit. Thereafter, the bubble point can be determined under continued elevation of the pressure. At the precise moment at which a continuous discharge of air bubbles can be seen on the nonpressurized side of the membrane, the pressure reached is read on the manometer. Taking account of the membrane properties, it is subsequently possible to calculate the largest pore and to estimate the retention property of the membrane.

In the abovementioned case, a filter medium which is oleophobic throughout is disadvantageous because simple homogeneous wetting is not possible with many organic solvents which are customary for the integrity tests.

The integrity (=faultless sealing of the filter medium in the filtration housing, largest pore for estimating retention properties) of filtration products having an oleophobic filter medium can be ascertained by determining the intrusion pressure. Here, the property of pressurized liquids whose surface tension is greater than that of the nonwetting porous system to enter the pores and penetrate them convectively upon attainment of a minimum pressure (=intrusion pressure) is utilized. The higher the intrusion pressure, the smaller the radius of the first penetrated largest pore. For this purpose, the filter-medium surface which is nonwetting under standard conditions (room temperature, atmospheric pressure) is completely overlaid with the test liquid. Similarly to the bubble-point method for ascertaining the bubble pass-through point on wetting systems, the liquid is applied with increasing pressure. Once test liquid appears on the nonpressurized side of the filter medium, the intrusion pressure has been reached, the level of which is a measure of the radius (diameter) of the largest pore in the oleophobic filter medium.

Using the same experimental setup, it is possible to carry out a pressure-hold test, in which the test liquid is applied at a pressure of about 80% of the intrusion pressure to be expected.

Oleophobic substances, which are distinguished by an especially high hydrophobicity, are not miscible or wettable with oils and other nonpolar substances. Their surface tension at 20° C. is less than 21 mN/m.

Water or purely aqueous solutions of salts (e.g. 0.9% NaCl, buffer) are processed in only a few applications. In many cases, there are water-based formulations containing not only inorganic salts but also wetting agents, organic solvents, proteins, vitamins and nutrients, which as a whole lower the surface tension of the solvent used and thus alter its wetting behavior with respect to solids. In these cases, it is recommended to contact the porous partition medium with the liquid for testing purposes in order to check the wetting behavior.

In the prior art, various methods for providing membranes having both hydrophobic and oleophobic properties have been described.

US 2008/0237117 A1 describes asymmetric membranes which have a multilayer structure and which consist of a hydrophobic base membrane. The hydrophobic base membrane can be formed from any desired hydrophobic polymers, for example from expanded PTFE.

The hydrophobic membrane has on one of its main surfaces a discontinuous coating which does not seal the pores and which is composed of an oleophobic polymer (e.g. a fluorinated polymer).

The membrane oleophobicized in such a one-sided manner can either have on its second opposing hydrophobic main surface a continuous, pore-covering, hydrophilic coating, or it is laminated via an adhesive onto a second hydrophobic membrane also having an oleophobic coating such that the two oleophobic coatings of the membrane composite point outward. US 2008/0237117 A1 describes neither membranes having gradually gradated hydrophobic properties across the membrane cross-section nor methods for preparing membranes having a hydrophobicity gradient.

WO 2009/065092 A1 discloses microporous textile-reinforced polyolefin membranes composed of PE, the main surfaces of which are selectively hydrophobicized or oleophobicized by means of an impregnation method.

The aforementioned impregnation method makes it possible to render a main surface of the microporous PE membrane oleophobic with a fluorine substituent-containing polymer, while the opposing main surface of the PE membrane retains its hydrophobic starting properties.

The disadvantages of these membranes known from WO 2009/065092 A1, which have proved themselves as a matter of principle as breathable materials in clothing manufacturing, are that they do not exhibit sufficient resistance to high-energy radiation, for example gamma radiation, and that they exhibit only insufficient temperature stability.

U.S. Pat. No. 5,554,414 discloses microporous composite membranes whose entire inner and outer surface is coated with a crosslinked polymer which is formed from a fluorine substituent-containing monomer and a crosslinker.

Coating the microporous membrane results in it not being wettable by a liquid having a surface tension of greater than 21 mN/m. U.S. Pat. No. 5,554,414 describes neither membranes having gradually gradated hydrophobic properties across the membrane cross-section (i.e. having a hydrophobicity gradient) nor methods for preparation thereof.

U.S. Pat. No. 6,579,342 B2 discloses venting filters whose hydrophobic base material (e.g. polysulfone or PVDF) is coated with an oleophobic oligomer which is functionalized with perfluoroalkyl groups and sulfone groups. The coating is applied to the surface of the base material by grafting the aforementioned oligomer. This document, too, does not disclose membranes having a hydrophobicity gradient.

In recent years, the trend toward single-use usage of plastic tanks in the processing of liquids has intensified. In contrast to metal tanks, tanks composed of organic polymers are not autoclaved for the purpose of sterilization, but are usually made pathogen-free for use by means of high-energy radiation, for example gamma radiation. Irradiation is a physical process which takes place at room temperature. The sterilizing (killing) action of the high-energy radiation is based on bond cleavage within the organic matter penetrated by gamma radiation.

Organic polymers are damaged to differing extents by high-energy radiation. Polytetrafluoroethylene (PTFE), polypropylene (PP) and polyvinyl chloride (PVC) in particular experience a dramatic weakening of their mechanical stability, whereas aromatic polymers such as polyether sulfones (polysulfone (PSU), polyethersulfone (PES)) and polyimides (PI) show only minor changes. Medium tolerance to gamma radiation is exhibited by, for example, polyethylene (PE), polyester (PET) and polyvinylidene fluoride (PVDF) (cf. table 1).

TABLE 1

| Organic polymer | Max. short-term usage temperature (° C.)** | Resistance range (kGy)* |
| --- | --- | --- |
| PTFE | 300 | 5 |
| POM | 150 | 15 |
| PP | 140 | 20 |
| PVC | 100 | 50 |
| PA 6.6 | 200 | 50 |
| PMMA | 100 | 100 |
| PE | 120 | 500 |
| PVDF | 150 | 1000 |
| PS | 90 | 1000 |
| PC | 160 | 1000 |
| PET | 200 | 1000 |
| PBT | 165 | 1000 |
| PEEK | 300 | 10 000 |
| PI | 400 | 10 000 |
| PAI | 300 | 10 000 |
| PSU | 170 | 10 000 |
| PES | 260 | 10 000 |

POM: polyoxymethylene;
PA 6.6: nylon 6,6, polyhexamethylene adipamide;
PMMA: polymethyl methacrylate;
PC: polycarbonate;
PAI: polyamide-imide;
PEEK: polyetheretherketone;
PS: polystyrene;
PBT: polybutylene terephthalate
*Resistance range in the case of gamma irradiation: data sheet from BGS (supplier: Beta-Gamma-Service GmbH & Co. KG, Fritz-Kotz-Strasse 16, 51674 Wiehl, Germany)
**Temperature values from "Saechtling Kunststoff Taschenbuch" ("Saechtling Plastics Handbook"), ed. K. Oberbach, C. Hanser Verlag, 27th edition, table 5.14

A summary of the material properties of currently commonly used porous partition media from table 1 reveals that none of the materials can satisfy the sum of the requirements and none can thus be used as a universal filter medium for sterile venting applications: hydrophobic PTFE exhibits, together with excellent temperature stability, minimal resistance to sterilizing radiation treatment. Hydrophobic PE is disadvantaged owing to low temperature stability and hydrophobic PP is disadvantaged owing to insufficient radiation resistance (cf. table 1).

In the case of polymers having a purely aliphatic main chain (e.g. PE, PTFE) or in the case of those having at least two consecutive saturated carbon atoms between aromatic chain segments (e.g. PET, PC), high-energy radiation leads to greater impairment of the mechanical strength thereof than in the case of aromatic main-chain polymers which are built up exclusively from aromatic building blocks, from an aromatic chain (e.g. PSU, PES) interrupted by only one nonaromatic main-chain atom or from aromatic building blocks which are linked to one another by means of a nonaromatic ring system.

The majority of the resistance ranges for gamma radiation, as described in the literature for polymeric materials, is based on mechanical measurements on solid shaped articles (e.g. data sheet from BGS (Beta-Gamma-Service, 51674 Wiehl, Germany)). Filter media are porous films or fibrous materials, the inner porosity of which is between 50% and 80%. The low material density of the pore-forming matrix increases the loss of strength of porous partition media owing to the damaging action of high-energy radiation.

It is an object of the present invention to provide a microporous membrane, the first external oleophobic main surface of which is not wettable with hydrophilic substances, such as lower alcohols (e.g. ethanol, isopropanol) or detergent-containing aqueous solutions, whereas the second external hydrophobic main surface of the membrane is wettable with the aforementioned hydrophilic substances and is amenable to an integrity test or being checked, wherein the membrane according to the invention allows, at the same time, temperature and radiation treatment.

SUMMARY OF THE INVENTION

This invention relates to a radiation-resistant microporous membrane having a hydrophobicity gradient from the first external main surface, through the membrane body toward the second external main surface, a method for the preparation thereof, and the use of the membrane in the sterilizing filtration of gaseous fluids or the use of the membrane as a liquid barrier in liquid-containing systems to be vented.

In the context of the present invention, microporous membranes are to be understood to mean membranes having a pore size between 0.01 to 10 µm.

DETAILED DESCRIPTION OF THE PREFERRED EMBODIMENTS

Figure 1:
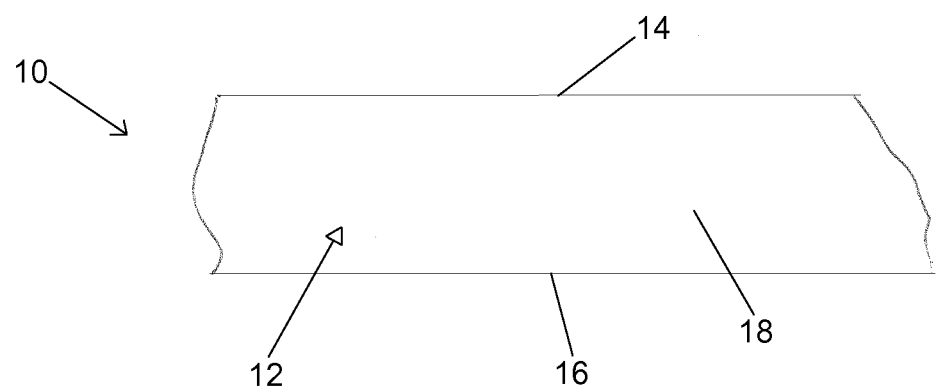
FIG. 1 is a schematic illustration of a membrane in accordance with the invention.

The microporous membrane according to the present invention is identified by the numeral 10 in FIG. 1 and is a microporous, radiation-resistant, temperature-resistant polymer membrane having a membrane body 12 with first and second external main surfaces 14 and 16 connected by means of the membrane body 12 via micropores 18, wherein the microporous membrane 10 has a hydrophobicity gradient from the first external main surface 14, through the membrane body 12, toward the second external main surface 16.

In a preferred embodiment of the membrane according to the invention, the first external main surface 14 is oleophobic and the second external main surface 16 is hydrophobic.

Owing to this combination of properties, the membrane 10 according to the invention is, in a particular way, suitable for the sterilizing filtration of gaseous fluids or as a liquid barrier for systems to be vented, because the upper first side 14 thereof, oleophobically, can be wetted neither by surfactant-containing solutions nor by lower alcohols (e.g. ethanol, isopropanol), whereas the hydrophobic second side 16 (underside) can be wetted with the aforementioned alcohols or surfactant-containing solutions in order to check the integrity (bubble-point test, pressure-hold test).

A preferred embodiment of the membrane 10 according to the invention exhibits a maximum short-term usage temperature of at least 125° C., particularly preferably at least 150° C. and most preferably at least 180° C. According to "Saechtling Kunststoff Taschenbuch", ed. K. Oberbach, C. Hanser Verlag, 27th edition, and according to the present invention, "maximum short-term usage temperature" is understood to mean the highest temperature up to which the membrane according to the invention can be transiently heated, without exhibiting a change in the mechanical properties thereof upon re-cooling to room temperature, i.e. the mechanical properties thereof after heating to the maximum short-term usage temperature and after cooling to room temperature correspond to the mechanical properties of a membrane according to the invention which has not been transiently heated to said usage temperature. Upon exceeding the maximum short-term usage temperature, however, changes in the mechanical properties occur.

Specifically, the present invention describes a microporous membrane 10, for example for the sterilizing filtration of gases or else as a liquid barrier for systems to be vented, a first main surface 14 of which has oleophobic properties, whereas the second main surface 16 thereof has hydrophobic properties, and which exhibits a maximum short-term usage temperature (cf. "Saechtling Kunststoff Taschenbuch", ed. K. Oberbach, C. Hanser Verlag, 27th edition) of greater than 125° C. and does not experience any detrimental reduction in mechanical properties owing to sterilizing gamma radiation at doses up to and including 50 kGy.

The membrane 10 according to the invention is sterilizable both by 20-minute treatment with superheated steam at 134° C. and by irradiation with pathogen-killing gamma radiation at a dose of 50 kGy. While years ago it was accepted, for example, to sterilize by means of superheated-steam treatment in an autoclave at 121° C. (corresponds to a positive pressure of 0.1 MPa), nowadays a temperature of 125° C. to 134° C. (corresponds to a positive pressure of 0.2 MPa) is used in order to kill microorganisms (especially in production plants) with sufficient certainty. This change in understanding of safety results in materials having a short-term maximum usage temperature of less than 125° C. ("Saechtling Kunststoff Taschenbuch", ed. K. Oberbach, C. Hanser Verlag, 27th edition, e.g. PVC, PS, PE, table 5.14) no longer being used.

In a preferred embodiment of the membrane 10 according to the invention, the loss of strength of the membrane 10 following gamma irradiation at a dose of 50 kGy is not more than 30%, preferably not more than 20% and particularly preferably not more than 10%. The loss of strength of the membrane 10 according to the invention comes from the decrease in the strength level of the membrane 10 following gamma irradiation at a dose of 50 kGy based on the strength level of the membrane prior to gamma irradiation at said dose. If the strength level of the irradiated membrane is 80% of the strength level of the nonirradiated membrane, the loss of strength is 20% according to the invention. In the context of the present invention, the strength levels of the irradiated and nonirradiated membranes are described in terms of their maximum tensile force values Fmax at room temperature (cf. tables 2A and 2B).

The membrane 10 according to the invention tolerates single and multiple sterilization by gamma radiation. Gamma irradiation is preferably carried out in collection containers which are moved around a radiation source over 4 to 8 hours to achieve a minimum dose of 50 kGy.

In the microporous membrane 10 of the present invention, the hydrophobicity gradient is preferably configured such that the hydrophobicity is maximum on the first external main surface 14 and decreases toward the second external main surface 16.

Alternatively, the hydrophobicity gradient can preferably be configured according to the invention such that the hydrophobicity is maximum on the first external main surface 14 of the microporous membrane 10, initially decreases toward the second external main surface 16, assumes a minimum within the microporous membrane body 12, but is still present, and subsequently increases toward the second external main surface 16, without reaching the maximum of the first external main surface 14.

In both abovementioned embodiments of the microporous membrane 10 according to the invention, the surface tension of the first external main surface 14 is less than 21 mN/m, whereas the surface tension of the second external main surface 16 is between 23 and 40 mN/m.

The hydrophobicity gradient present in the microporous membrane 10 according to the present invention is preferably generated by the presence of a fluorine-containing organic compound. In the microporous membrane 10 according to the invention, the gradient in fluorine content, caused by the presence of the fluorine-containing organic compound, within the membrane body as an indicator for the hydrophobicity gradient can be ascertained by EDX analysis (energy-dispersive X-ray spectroscopy).

EDX analysis utilizes the characteristic high-energy electromagnetic radiation (=X-radiation) which elements emit upon electron bombardment. The radiation is released when an inner shell electron, following collision with an exogenous electron, falls back into the inner K or L shell. The energy being released in the form of high-frequency electromagnetic oscillation is specific for the element to be analyzed (in this case, fluorine) and can be analyzed by external detectors. The EDX analysis method makes it possible to detect the hydrophobicity gradient of the membrane according to the invention, which runs through the membrane body from the first external main surface toward the second external main surface, as atomic distribution in atom % of the fluorine substituents of the fluorine-containing organic compound (cf. FIG. 1).

The above-described fluorine-containing organic compound is preferably present in the form of a fluorine substituent-containing polymer fixed on the microporous membrane.

In an alternative embodiment of the membrane 10 according to the invention, the fluorine-containing organic compound is a reaction product of a monomeric, oligomeric or polymeric fluorine-containing compound with reactive groups of the starting material of the polymer membrane.

The depth of penetration (pore size of the starting material of the polymer membrane vs. particle size of the fluorine-containing compound) of the underlying monomeric, oligomeric or polymeric fluorine-containing compound into the starting material of the polymer membrane determines the fluorine distribution and thus the hydrophobicity gradient in the microporous membrane according to the invention.

Particular preference is given to embodiments in which the first external main surface 14 of the membrane 10 according to the invention is oleophobic and the first main surface 14 contains the fluorine-containing compound at a higher concentration compared to the second external hydrophobic main surface 16 and compared to the microporous membrane body 12, and so the first external main surface 14 is only wettable with liquids having a surface tension of less than 21 mN/m, whereas the second external main surface 16 and the surface within the membrane body 12 are wettable by means of liquids having a surface tension of no more than 40 mN/m.

In a preferred embodiment of the invention, the starting material of the polymer membrane consists of PVDF, PSU (polysulfone), PES (polyethersulfone), PPS (polyphenylene sulfide), PBI (polybenzimidazole), PEEK or PAI.

In a particularly preferred embodiment of the invention, the polymer membrane comprises at least one aromatic main-chain polymer. Most preferably, the aromatic main-chain polymer is selected from the group of PSU, PES or mixtures thereof.

The microporous membrane 10 according to the invention preferably has a thickness of between 50 and 250 µm and is preferably in the form of web material. The pore 18 size is between 0.01 and 10 µm.

The method for preparing a microporous membrane 10 according to the present invention comprises the steps of impregnating the microporous membrane through one of its two main surfaces 14, 16 with a fluorine-containing organic compound and heating the microporous membrane 10.

The hydrophobicity gradient according to the invention of the microporous membrane 10 is brought about, for example, by impregnating the membrane with a reactive textile auxiliary agent and subsequently drying and cross-linking at temperatures in the range from 125° C. to 200° C. Reactive textile auxiliary agents for bringing about an oil-repelling effect contain fluorocarbon compounds which are applied to the fibers of the textile and are hardened as a coating on the fiber surface at an elevated temperature.

For example, the planar microporous membrane 10 impregnated with the textile auxiliary agent is dried and subsequently brought to a drying temperature in the range from 120 to 150° C., for example 135° C., at which the deposited reactive substances melt.

Thereafter, a posttreatment temperature in the range from 150 to 200° C., for example 170° C., is reached, at which the reactive groups of the molten substances become activated and, during sufficient residence time at the posttreatment temperature, enter into a crosslinking reaction.

Thereafter, the external main surfaces 14, 16 of the thus treated porous planar membrane 10 exhibit different surface tensions, wherein the main surface having the higher amount of textile auxiliary agent exhibits a lower surface tension than the main surface having the lower amount of textile auxiliary agent.

Lastly, the present invention provides for the use of the microporous membrane 10 according to the invention in the sterilizing filtration of gaseous fluids and for the use of the microporous membranes according to the invention as a liquid barrier in liquid-containing systems to be vented.

The present invention provides a microporous membrane 10 having a first external oleophobic main surface 14 and a second external hydrophobic main surface 16, the first external oleophobic main surface 14 of which is not wettable with hydrophilic substances, such as lower alcohols (e.g. ethanol, isopropanol) or detergent-containing aqueous solutions, whereas the second external hydrophobic main surface 16 of the membrane is wettable with the aforementioned hydrophilic substances and is amenable to an integrity test or being checked, wherein the membrane 10 according to the invention allows, at the same time, temperature and radiation treatment. This allows the microporous membrane 10 according to the invention to be advantageously used in sterilizing filtration of gaseous fluids, for example at at least one tank opening (a flange) as part of a sterile-filtering venting element (venting device) or as a liquid barrier for liquid-containing systems to be vented in order to prevent damage to the manufacturing equipment due to elevated or reduced pressure and, at the same time, if necessary for sterile applications, to ensure that the solution-contacted interior is pathogen-free during venting. On the one hand, the microporous membrane 10 is not wetted, on its oleophobic side 14 facing the tank interior, by the solution and the ingredients thereof situated in the interior and thus remains gas-permeable. On the other hand, the hydrophobic external side 16 (i.e. the second external main surface 16) of the microporous membrane 10 according to the invention further provides the possibility of carrying out integrity tests in the form of a pressure-hold test and/or bubble-point test. At the same time, such an arrangement comprising the microporous membrane 10 according to the invention is advantageously suitable for single use (e.g. in disposable plastic pouches having sterile venting filters) for sterilization by means of gamma irradiation. Despite the modification according to the invention of the microporous membrane 10 by means of a hydrophobicity gradient, the membrane 10 has, furthermore, sufficient air permeability in the end use. The present invention and further resulting advantages will be more particularly elucidated with reference to the embodiments described in the examples, without restricting the scope of the claims for which protection is sought to said embodiments.

EXAMPLES

Example 1

The first external main surface of a hydrophobic 0.2 μm microfiltration membrane composed of PVDF (Millipore, model GVHP) is impregnated at room temperature by placement for 5 seconds on a diluted NUVA 3049 liq (Clariant, 30% strength) dispersion, consisting of 8 parts by volume of 30% strength NUVA, 95 parts by volume of water and 20 parts by volume of 2-propanol. The wetted membrane sample is then completely immersed in the dispersion for a further 15 seconds, and subsequently held upright in the air for 1 minute to allow excess impregnation liquid to drain off. The second external surface of the thus impregnated microfiltration membrane is placed onto a heated plate and dried at 125° C. and subsequently posttreated at 150° C. for 10 minutes. The first external surface, which is oleophobic after heat treatment, is not wetted by pure 2-propanol. The second external surface and the inner surface of the treated membrane sample exhibit spontaneous homogeneous wetting with 2-propanol.

Example 2

The fine-pored side of an asymmetric hydrophobic 0.2 μm microfiltration membrane composed of polysulfone (PSU, Sartorius Stedim Biotech GmbH, model 14907) is wetted by placement on a diluted NUVA 3049 liq (Clariant) dispersion, consisting of 6 parts by volume of 30% strength NUVA, 94 parts by volume of water and 20 parts by volume of ethanol, dried according to example 1, and subsequently posttreated at a temperature of 170° C. The thus obtained PSU microfiltration membrane, which is oleophobic on one side, wets spontaneously with ethanol on the underside (on the untreated, nonimpregnated main surface); on the treated, impregnated surface, ethanol drips off.

Example 3

A microporous 0.2 μm PES membrane (Sartorius Stedim Biotech GmbH, model 15407) wettable with water is wetted by placement on a diluted NUVA 3049 liq dispersion, consisting of 5 parts of 30% strength NUVA and 105 parts of water, and treated according to example 1, wherein the posttreatment is carried out at 180° C., in order to subsequently obtain a membrane which is oleophobic on one side.

Determination of the loss of strength upon gamma irradiation at a dose of 50 kGy for membranes according to the invention as per examples 2 and 3 and for comparative samples To determine the loss of strength following gamma irradiation at a dose of 50 kGy, a rectangular membrane cutting (1st membrane cutting: membrane with no gamma irradiation treatment; 2nd membrane cutting: membrane following gamma irradiation at 50 kGy) is clamped lengthwise into the vertically arranged (on top of one another) retainers (clamping jaws) of a measuring apparatus described in more detail below. The upper clamping jaw is connected to a force transducer, which in turn can be moved vertically at a constant velocity (spindle drive). The characteristic observation value used is the maximum tensile force Fmax for the stretching of the tightly clamped membrane.

For this purpose, a membrane sample measuring 20 mm×150 mm is cut and clamped horizontally into a "Zwick Z2.5/TN1S" materials testing machine from Zwick GmbH such that the free sample length between the clamping jaws is 4 cm. The force transducer "KAP-Z 200N", A.S.T., 01287 Dresden, Germany, is moved at a velocity of, for example, 5 cm/min. The measurement data are continuously recorded and visualized by the instrument software "testXpert", Zwick GmbH, 89079 Ulm, Germany. $F_{max}$ is determined as the mean value of three irradiated membrane samples and of three nonirradiated membrane samples (cf. table 2A and table 2B).

TABLE 2A

| Sample | Sample no. |
|---|---|
| PTFE-MF 0.2 μm (Gore Microfiltration Media, USA, model S30189) | 1) |
| PA-MF 0.2 μm (Sartorius Stedim Biotech, Germany, model 25007) | 2) |
| PP-MF 0.2 μm (Membrana, Germany, model 2 EHF 6037) | 3) |
| PVDF-MF 0.22 μm (Millipore Corp., USA, model GVHP) | 4) |
| PVDF-MF 0.22 μm as per example 1 (Millipore Corp., USA, model GVHP) | 5) |
| PE blown film | 6) |
| PPS nonwoven 120 μm (Carl Freudenberg, Germany, model FO2440-608243) | 7) |
| PET nonwoven 110 μm (Hirose, Japan, model 05-TH80) | 8) |
| PET film 50 μm (Pütz, Germany, model Hostaphan RN) | 9) |
| PSU-MF 0.2 μm (Sartorius Stedim Biotech, Germany, model 14907) | 10) |
| PSU-MF 0.2 μm as per example 2 (Sartorius Stedim Biotech, Germany, model 14907 OB) | 11) |
| PES-MF 0.2 μm (Sartorius Stedim Biotech, Germany, model 15407) | 12) |
| PES-MF 0.2 μm as per example 3 (Sartorius Stedim Biotech, Germany, model 15407 OB) | 13) |

TABLE 2B

| | $F_{max}$/[N] | | Change in $F_{max}$ |
|---|---|---|---|
| Sample no. | Nonirradiated | Irradiated, 50 kGy | % |
| 1) | 10.6 | 1.1 | −90.0 |
| 2) | 17.5 | 9.9 | −43.3 |
| 3) | 4.5 | 2.6 | −41.7 |
| 4) | 12.7 | 10.6 | −16.3 |
| 5) | 12.6 | 10.1 | −19.8 |
| 6) | 25.6 | 24.5 | −4.2 |
| 7) | 86.4 | 83.5 | −3.4 |
| 8) | 98.4 | 105.1 | 6.8 |
| 9) | 130.5 | 126.9 | −2.8 |
| 10) | 8.2 | 8.4 | 2.3 |
| 11) | 9.1 | 9.2 | 1.1 |
| 12) | 12.5 | 12.2 | −2.2 |
| 13) | 15.0 | 15.4 | 2.3 |

For the membranes according to the invention as per examples 1, 2 and 3 (sample numbers 5), 11) and 13)), the loss of strength following gamma irradiation at a dose of 50 kGy is below 20% based on the nonirradiated membrane, and for the membranes according to the invention based on polysulfone and polyethersulfone, a slight increase in the strength level of 1.1% and 2.3%, respectively, compared to the nonirradiated membrane is even observed.

Wetting Behavior of the Membranes According to the Invention with Water, Aqueous Solutions of NaCl (0.9% by Weight) or of a Detergent (1% by Weight) or Water-Ethanol Mixtures Results for the wetting behavior of various microporous (0.2 μm) sterile-filtering membrane filters are determined visually as described below and are shown in table 3. The membrane sample is placed onto a milk glass plate illuminated from the reverse side. Using a pipet, a 50 μl drop of liquid is applied to the horizontal external oleophobic main surface of the membrane sample. Said oleophobic main surface is, in the case of the membrane according to the invention of example 3, the main surface through which the membrane has been impregnated with the fluorine-containing organic compound in the first step of the method according to the invention as per example 3.

"Wetted" (W): Liquid has entered the inner surface. The membrane sample appears brighter in the wetted region. If, after 60 seconds, there is no wetting of the membrane sample, the drop of liquid is sucked up using a pipet. "Film" (F): Upon aspiration of the liquid, a film remains on the surface, and the liquid spreads on the surface and does not enter the inner surface.

"Drop" (D): Liquid remains lying on the surface as a drop, and can be completely aspirated. There is no wetting of the membrane.

TABLE 3

| Material, 0.2 μm | Surface tension σ [mN/m] | $H_2O$ | 0.9% NaCl | 1% Detergent | 5% EtOH | 20% EtOH | 50% EtOH | 98% EtOH |
|---|---|---|---|---|---|---|---|---|
| PES, hydrophilic* | — | W | W | W | W | W | W | W |
| PSU | — | D | D | F | F | F | W | W |
| PVDF | 33.7 | D | D | F | D | F | W | W |
| PP | 32 | D | D | F | D | F | W | W |
| PTFE | 22.5 | D | D |  | D | D | F | W |
| PES, treated** | 21 | D | D | D | D | D | D | D |

All percentages for NaCl and EtOH are percentages by weight for an aqueous saline solution and for ethanol in an ethanol-water mixture, respectively.
* Starting membrane of example 3
** Membrane according to the invention prepared as per the method according to the invention of example 3 having a hydrophobicity gradient Detection of the Hydrophobicity Gradient in the Membrane According to the Invention as Per Example 3 Using EDX Analysis The electron bombardment of a nonconductively vapor-coated membrane sample according to the invention as per example 3 is carried out at an acceleration voltage of 7.5 kV in the vacuum chamber of an electron microscope from Fei, model "Quanta 200 FEG" in the "low-vacuum mode" at 0.1-1 Torr. The EDX detector, from EDAX, introduced into the chamber is a liquid nitrogen-cooled, lithium-doped silicon crystal. The analysis software used is the program "Genesis" from EDAX.

To analyze the fluorine content of a surface, the second external hydrophobic main surface, and the inner surface spread out between the two external main surfaces, of the membrane according to the invention are wetted with a C1 to C3 alkanol, for example with 2-propanol, and broken in liquid nitrogen. The break surface, i.e. the cross-sectional area of the membrane between the two external main surfaces, is positioned in the vacuum chamber of a scanning electron microscope (SEM) and enlarged such that the external main surfaces no longer appear in the search range of the scanning electron beam. The EDX detector records the high-frequency signals of the atoms struck by the beam of the SEM. The discrete frequencies and the incidence thereof are assigned by the software and shown as a distribution of the fluorine atoms across the membrane cross section (cf. FIG. 1). The values in atom % (EDAX software) are mean values of the fluorine measurements in three 10×10 μm measurement windows lying adjacent to one another at the same height.

For the two-point calibration of the measurement results obtained, a starting membrane not treated with a fluorine compound (e.g. PES; fluorine content 0%) and a fluorine-containing membrane (e.g. PTFE, fluorine content 34%) are analyzed consecutively according to the detection method described.

The first external main surface of the membrane as per example 3 shows the highest fluorine content (1.5 atom %), whereas, within the membrane body, the fluorine content drops to a minimum value of below 0.2 atom %, in order to rise to 0.8 atom % on the second external hydrophobic main surface.

Figure 2:
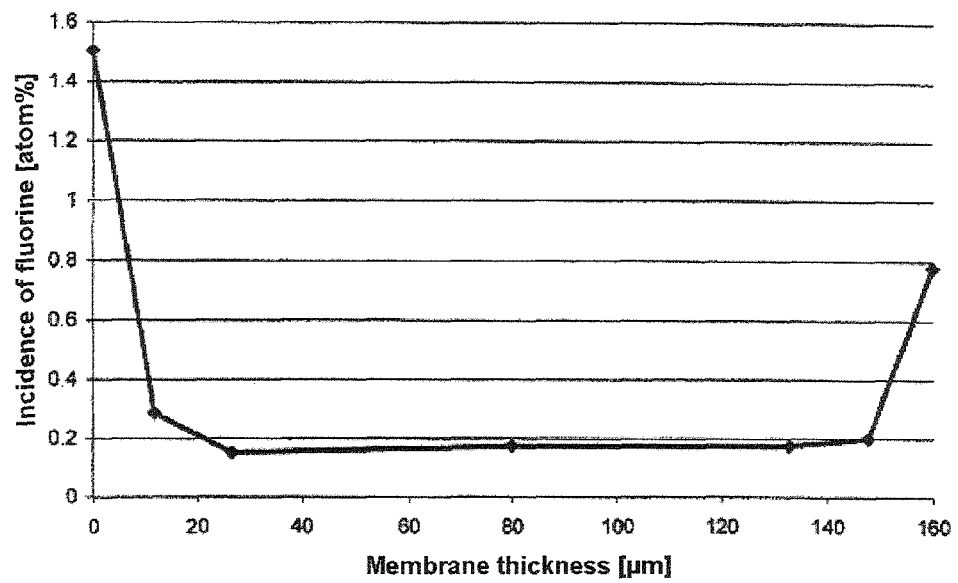
FIG. 2 is a graph summarizing the data in Tables 2A, 2B and 3.

The results in tables 2A, 2B and 3 in conjunction with FIG. 2 provide evidence that the membranes according to the invention, owing to their hydrophobicity gradient, are not wettable with hydrophilic substances (such as lower alcohols (e.g. ethanol, isopropanol), detergent-containing aqueous solutions) on their first external oleophobic main surface, but are wettable with the aforementioned hydrophilic substances on their second external hydrophobic main surface and are amenable to an integrity test or being checked. At the same time, associated with this advantageous hydrophobicity gradient is high temperature and gamma-irradiation resistance, which predestines the membrane especially for use in sterile disposable applications in biotechnology.

The invention claimed is:

1. A microporous, gamma radiation-resistant, temperature-resistant polymer membrane having a membrane body with first and second external main surfaces connected by micropores in the membrane body, wherein the microporous membrane has an asymmetric hydrophobicity gradient from the first external main surface, through the membrane body, toward the second external main surface, the asymmetric hydrophobicity gradient is configured such that the hydrophobicity is maximum on the first external main surface, initially decreases toward the second external main surface, assumes a minimum within the microporous membrane body, but is still present, and subsequently increases toward the second external main surface, without reaching the maximum of the first external main surface, and wherein a loss of strength of the polymer membrane owing to sterilization by γ-irradiation at a dose of 50 kGy is not more than 20%.

2. The microporous polymer membrane of claim 1, wherein the polymer membrane is heatable to 150° C. and subsequently coolable to room temperature without changing mechanical properties thereof.

3. The microporous membrane of claim 1, wherein the asymmetric hydrophobicity gradient is configured such that the first external main surface is an oleophobic surface that cannot be wetted by surfactant-containing solutions and lower alcohols, whereas the hydrophobic second external main surface can be wetted by surfactant-containing solutions and lower alcohols.

4. The microporous membrane according of claim 1, wherein the surface tension of the first main surface is less than 21 mN/m and the surface tension of the second main surface is between 23 and 40 mN/m.

5. The microporous membrane of claim 1, wherein the asymmetric hydrophobicity gradient is generated by the presence of a fluorine-containing organic compound.

6. The microporous membrane of claim 5, wherein the fluorine-containing organic compound is present in the form of a fluorine substituent-containing polymer fixed on the microporous membrane.

7. The microporous membrane of claim 5, wherein the fluorine-containing compound is a reaction product of a monomeric, oligomeric or polymeric fluorine-containing compound with reactive groups of the starting material of the polymer membrane.

8. The microporous membrane of claim 1, wherein the polymer membrane comprises at least one aromatic main-chain polymer.

9. The microporous membrane of claim 8, wherein the aromatic main-chain polymer is selected from the group of polysulfone, polyethersulfone or mixtures thereof.

10. A method for preparing a microporous radiation-resistant, temperature resistant polymer membrane having a membrane body with two external main surfaces connected by micropores in the membrane body, wherein the microporous membrane has an asymmetric hydrophobicity gradient from the first external main surface, through the membrane body, toward the second external main surface, comprising the steps of:
  impregnating the microporous membrane through the first external main surface with a fluorine-containing organic compound;
  drying the impregnated microporous membrane to a drying temperature in a range of 120° C. to 150° C.;
  heating the dried microporous membrane to a posttreatment temperature in a range of 150° C. to 200° C. for a sufficient time to achieve a crosslinking reaction, wherein the asymmetric hydrophobicity gradient is such that the hydrophobicity is maximum on the first external main surface, initially decreases toward the second external main surface, assumes a minimum within the microporous membrane body, but is still present, and subsequently increases toward the second external main surface, without reaching the maximum of the first external main surface; and
  sterilizing the dried microporous membrane by γ-irradiation at a dose of 50 kGy.

11. A method of using the microporous membrane of claim 1 in the sterilizing filtration of gaseous fluids, comprising:
  positioning the microporous membrane with the first surface facing toward the gaseous fluids being sterilized;
  carrying out the sterilizing while preventing wetting of the membrane due to the hydrophobicity gradient from the first external main surface, through the membrane body, and toward the second external main surface; and
  allowing venting of gaseous media through the membrane.

12. A method of using the microporous membrane of claim 1 as a liquid barrier in liquid-containing system that includes a container to be vented, comprising:
  positioning the membrane across an opening to the container with the first surface of the membrane facing into the container; and
  allowing gaseous media in the container to be vented while preventing the membrane from being wetted by the liquid in the container.

* * * * *